US008894597B2

(12) United States Patent
Newkirk (10) Patent No.: US 8,894,597 B2
(45) Date of Patent: Nov. 25, 2014

(54) SCAPULO-SPINAL STABILIZER WITH ABDOMINAL SUPPORT FOR OPENING THE SUPERIOR THORACIC APERTURE

(76) Inventor: Tracy A. Newkirk, Mill Valley, CA (US)

( * ) Notice: Subject to any disclaimer, the term of this patent is extended or adjusted under 35 U.S.C. 154(b) by 420 days.

(21) Appl. No.: 13/226,388

(22) Filed: Sep. 6, 2011

(65) Prior Publication Data

US 2012/0059297 A1    Mar. 8, 2012

Related U.S. Application Data

(60) Provisional application No. 61/380,218, filed on Sep. 4, 2010.

(51) Int. Cl.
*A61F 5/28* (2006.01)
*A61F 5/00* (2006.01)
*A41D 13/00* (2006.01)
*A61F 5/02* (2006.01)

(52) U.S. Cl.
CPC ............... *A61F 5/026* (2013.01); *A61F 5/028* (2013.01)
USPC ................................... 602/19; 2/69; 128/99.1

(58) Field of Classification Search
USPC ............ 128/100.1, 99.1, 96.1, 845, 846, 847, 128/869, 873, 874; 602/19, 5, 20, 4, 32, 36, 602/6, 13; 2/114, 8, 102, 693, 44, 45, 115, 2/104
See application file for complete search history.

(56) References Cited

U.S. PATENT DOCUMENTS

| | | | | |
|---|---|---|---|---|
| 1,587,716 A * | 6/1926 | Fritsch | ................. | 2/44 |
| 2,421,736 A * | 6/1947 | Wein | ................. | 2/268 |
| 4,099,524 A * | 7/1978 | Cueman et al. | ................. | 602/19 |
| 7,392,549 B1 * | 7/2008 | Barber | ................. | 2/86 |
| 7,871,388 B2 * | 1/2011 | Brown | ................. | 602/19 |
| 2007/0073204 A1 * | 3/2007 | Suarez et al. | ................. | 602/19 |

* cited by examiner

*Primary Examiner* — Patricia Bianco
*Assistant Examiner* — Tarla Patel
(74) *Attorney, Agent, or Firm* — Brian Beverly; Beeson Skinner Beverly, LLP (57) ABSTRACT

A scapulo-spinal stabilizer with abdominal support for opening the superior thoracic aperture comprises a shirt-like garment for wearing on the torso, the garment having two elongated, semi-rigid thoraco-lumbar support stays disposed in dual, parallel sheaths in a posterior panel thereof, two posterior flexible scapular straps anchored on and angularly depending from superior shoulder portions of the garment, the scapular straps forming a posterior crossing configuration across the support stays, and anterior ends of the scapular straps detachably attached to opposite lateral ends of an anterior rib margin support disposed on the anterior portion of the garment, the scapular stays, scapular straps and anterior rib margin support stabilizing the posture of a wearer and opening the superior thoracic aperture.

15 Claims, 11 Drawing Sheets

Top Closed   FIG. 9A

Rear Closed   FIG. 9B

Shoulders hunched forward   FIG. 9C

Top Open  FIG. 10A

Rear Open  FIG. 10B

Shoulders pulled back  FIG. 10C

FIG. 11

SCAPULO-SPINAL STABILIZER WITH ABDOMINAL SUPPORT FOR OPENING THE SUPERIOR THORACIC APERTURE

CROSS-REFERENCE TO RELATED APPLICATIONS

This application claims the benefit of U.S. Provisional Application No. 61/380,218 filed Sep. 4, 2010.

BACKGROUND

1. Field of the Invention

This invention relates to devices for improving body posture or for supporting or stabilizing body features, in particular to a garment for stabilizing and bringing into beneficial anatomical arrangement the scapulo-spinal region, and most particularly for opening the superior thoracic aperture.

2. Prior Art

The use and evolution of postural devices to attempt to correct body posture, with or without recognized structural skeletal or muscular defects, is ancient. Much work remains to be done which will allow presentation of a flexible device that improves degraded posture as well as pathologic postural problems without restricting normal function. Tolerability is a major concern for such devices.

SUMMARY OF THE INVENTION

Figure 9A:
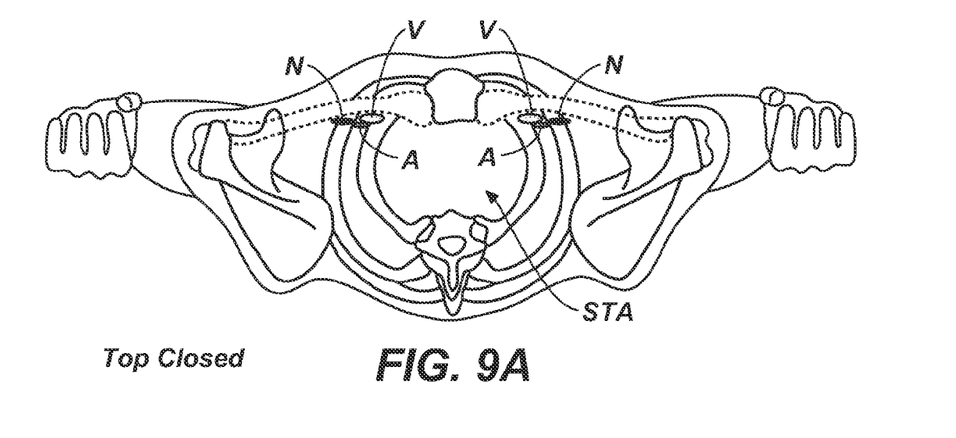
FIG. 9A is a top view of the anatomy surrounding the superior thoracic aperture showing the top of the aperture closed.
Figure 9B:
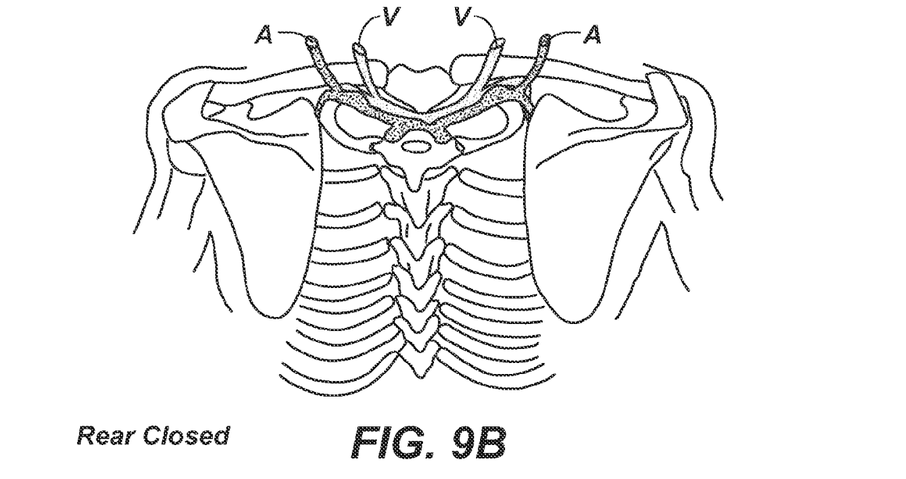
FIG. 9B is rear view of the anatomy surrounding the superior thoracic aperture showing the top of the aperture closed.
Figure 9C:
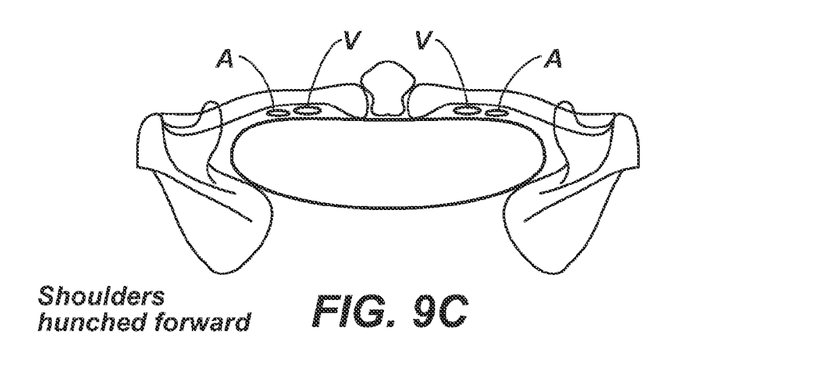
FIG. 9C is a simplified graphical representation of the bone structure adjacent the superior thoracic aperture showing the veins and arteries compressed.
Figure 10A:
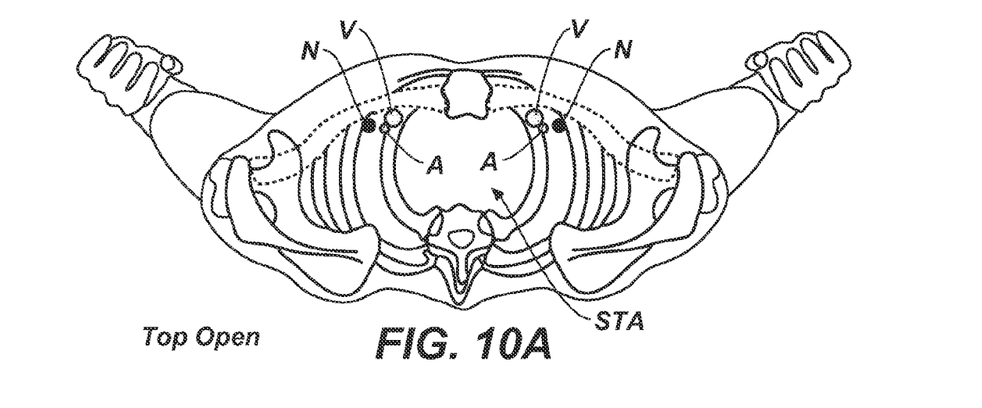
FIG. 10A is a top view of the anatomy surrounding the superior thoracic aperture showing the top of the aperture open.
Figure 10B:
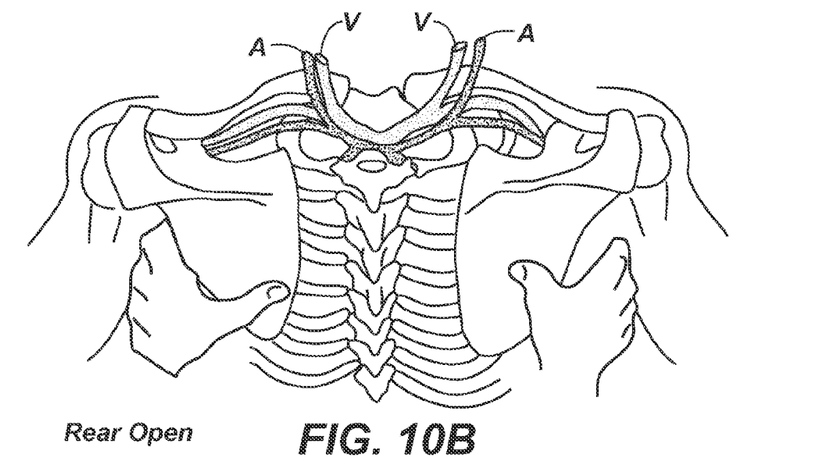
FIG. 10B is rear view the anatomy surrounding the superior thoracic aperture showing the top of the aperture open.
Figure 10C:
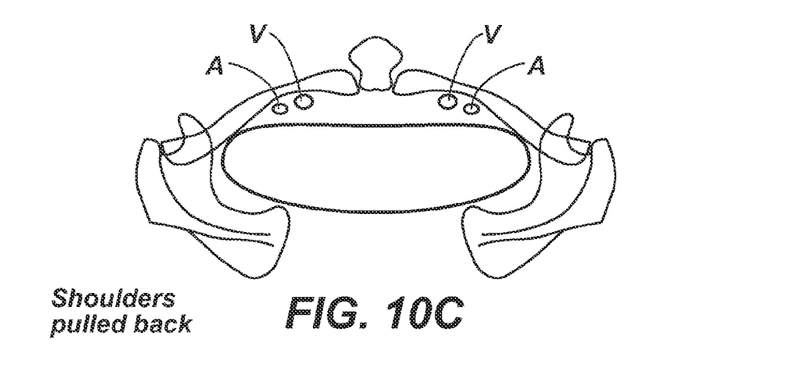
FIG. 10C is a simplified graphical representation of the bone structure adjacent the superior thoracic aperture showing the veins and arteries uncompressed and fully open.

A scapulo-spinal stabilizer according to the invention attempts to meet those requirements while preserving normal blood flow and redistributing body weight in a normal fashion along the spinal axis. FIGS. 9A-9C are views of the anatomy surrounding the superior thoracic aperture and show that when the shoulders are hunched forward the arteries, veins and nerves A, V, N passing through the superior thoracic aperture STA are compressed by the restricted size of the aperture. FIGS. 10A-10C are views similar to FIGS. 9A-9C showing that the arteries, veins and nerves A, V, N are released from compression, increasing blood flow, when the superior thoracic aperture STA is opened up.

The invention is a flexible, shirt-like garment that may be worn with or without sleeves. It is composed of expansible polyurethane fabric or a latex-embedded material utilizing a front-closing zipper, hook-and-loop type fasteners, stabilizers that appose the zipper components allowing freedom to close the zipper, and a zipper cord that holds the garment vertically stable while closing the zipper. The vest adducts the scapulae and simultaneously lifts the xiphisternum, thus increasing the front-to-back diameter of the superior thoracic aperture and the thoracic cage. Shoulder blade containment straps are provided that are contiguous anteriorly with a line of force that elevates the xiphisternum. The vest stretches the scalene muscles, relieves compression of the brachial plexus, improves venous return from the head, spinal cord, arms and chest, improves rib motion, expands respiratory volume and improves lymphatic flow from the head, chest and arms.

BRIEF DESCRIPTION OF THE ILLUSTRATIONS

DETAILED DESCRIPTION OF THE ILLUSTRATED EMBODIMENT

Figure 1:
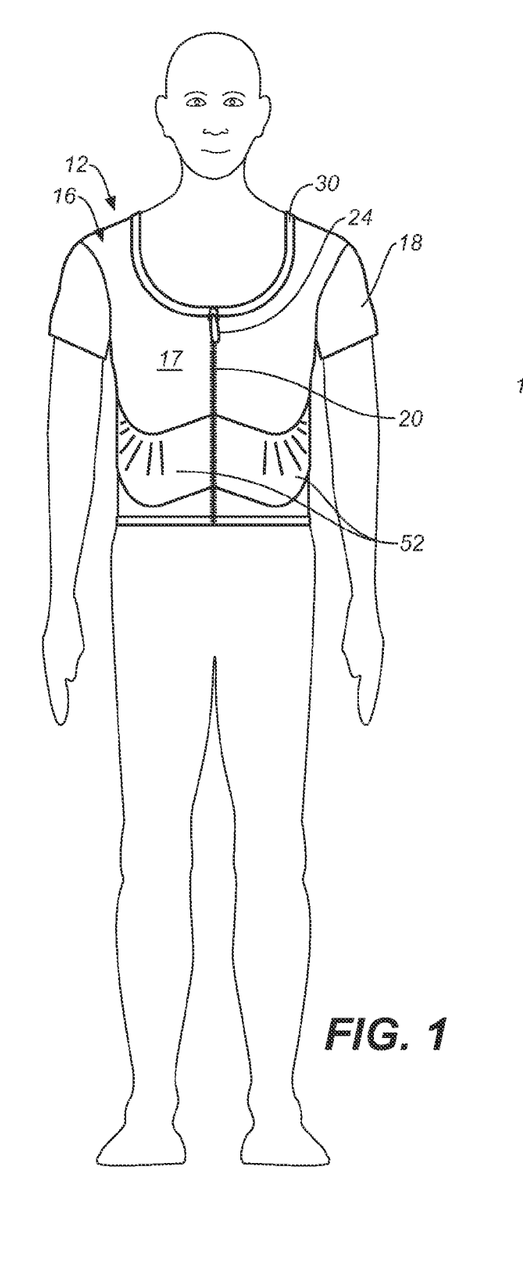
FIG. 1 is a front elevational view of a scapulo-spinal stabilizer according to the invention shown being worn by an individual.
Figure 5A:
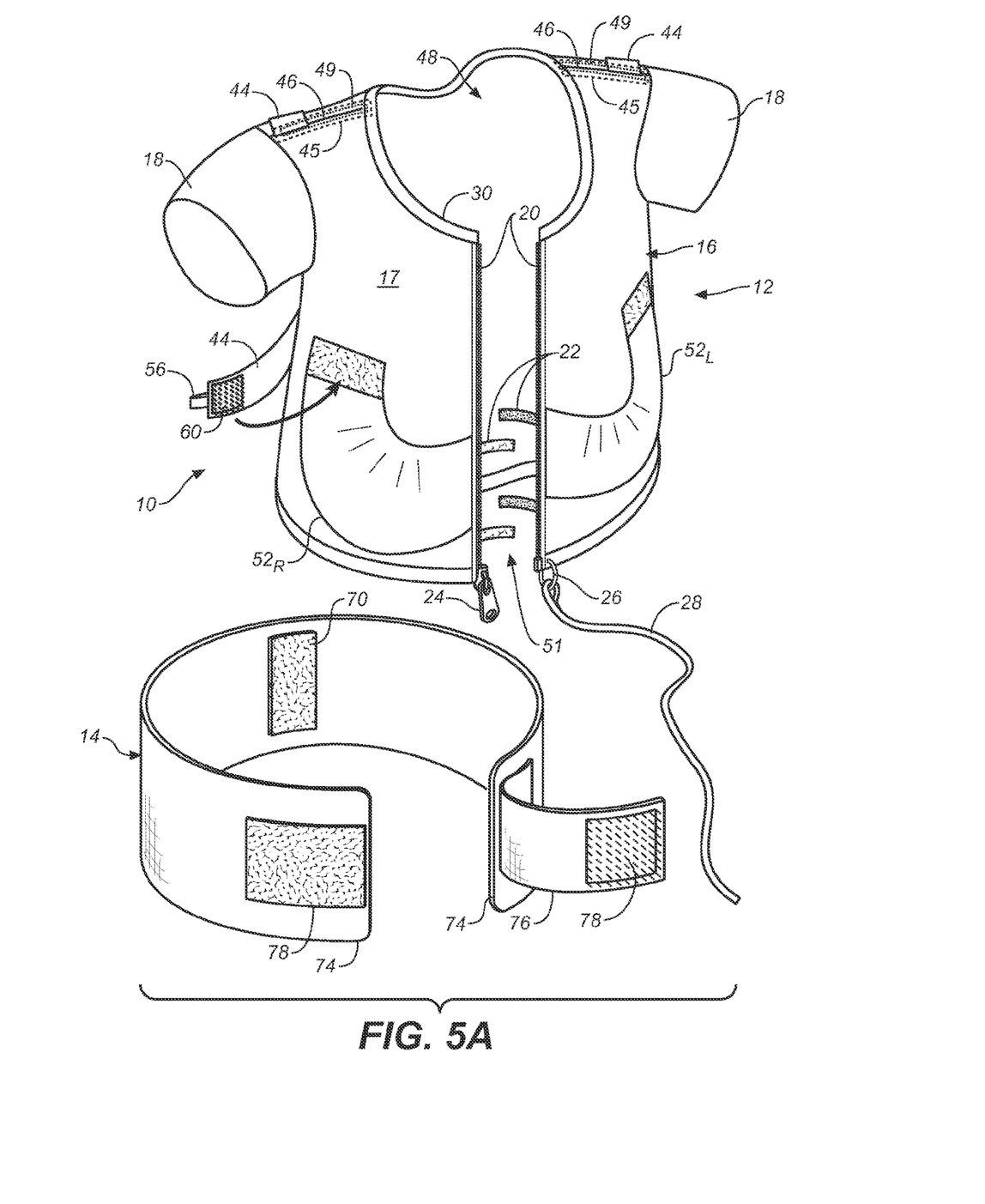
FIG. 5A is an exploded front upper perspective view of a scapulo-spinal stabilizer with the front of the vest open to reveal pull tabs extending from the inner edges of the inferior anterior rib margin support bands, and showing the waist band closure open.
Figure 5B:
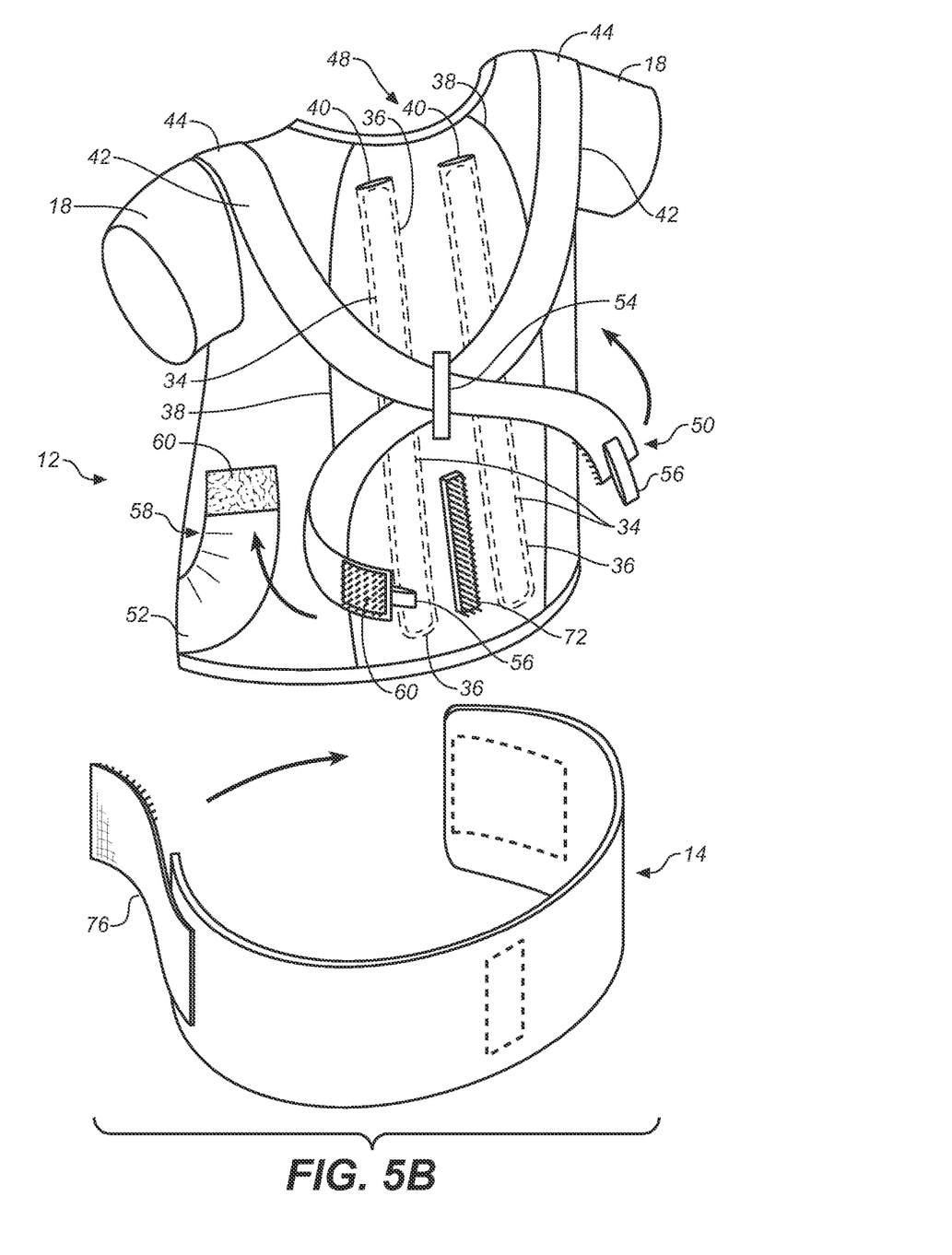
FIG. 5B is an exploded rear upper perspective view of the scapulo-spinal stabilizer shown in FIG. 5A with the ends of the scapular cross straps detached from the upper ends of the inferior anterior rib margin support bands, and showing the waist band closure open.

A scapulo-spinal stabilizer with abdominal support 10 is shown in FIGS. 5A and 5B. The invention comprises a vest 12 and a waist band 14. The vest is comprised of a fitted shirt-like garment 16 extending approximately from the upper torso to the iliac crest. The garment 16 is composed of an expansible polyurethane fabric or a latex-embedded material, such as is available under the Lycra® brand. In one embodiment the anterior portion is constructed of non-elastic material. Sleeves 18 which wrap around the distal arms are optionally provided as a stabilizing element for minimizing the posterior pull of scapular cross-straps 42 (discussed below) on the anchor points 44 behind the acromioclavicular (A-C) joint, thereby maintaining correct positioning of the straps 42. Sleeves 18 are constructed of a lighter or more silken polyurethane fabric than the main body of the garment. A zipper 20 forms a front closure in the anterior portion 17 of the garment. One or more pairs of cooperating tabs 22 having hook-and-loop type fasteners extend laterally from the left and right sides of the anterior portion of the garment 16. Fastening together of cooperating pairs of tabs 22 permits securement of the left and right sides of the anterior portion 17 in close adjacency to each other, but while still being spaced apart, in preparation for closing the zipper 20. Tabs 22 help overcome elasticity of the garment and align the opposing teeth of the zipper 20 to facilitate closing the zipper. Once the zipper 20 is closed, the tabs are hidden under the garment. See FIG. 1. The vest 12 is provided with a ring 26 at or immediately adjacent to the bottom of the zipper to which can be temporarily attached a zipper leash 28 (see FIG. 5A) that drops to the floor. A person donning the vest 12 may then step on the cord thereby stabilizing the zipper lining and making it easier to pull up the zipper pull 24 to close the zipper 20. The zipper leash 28 may then optionally be detached, or left attached, and stored inside the waist band 14. This is of benefit for individuals who have arthritis of the fingers or diminished pinch strength. The front neckline 30 of the garment 16 may be scooped so that it is hidden when worn under a shirt or blouse.

Figure 2:
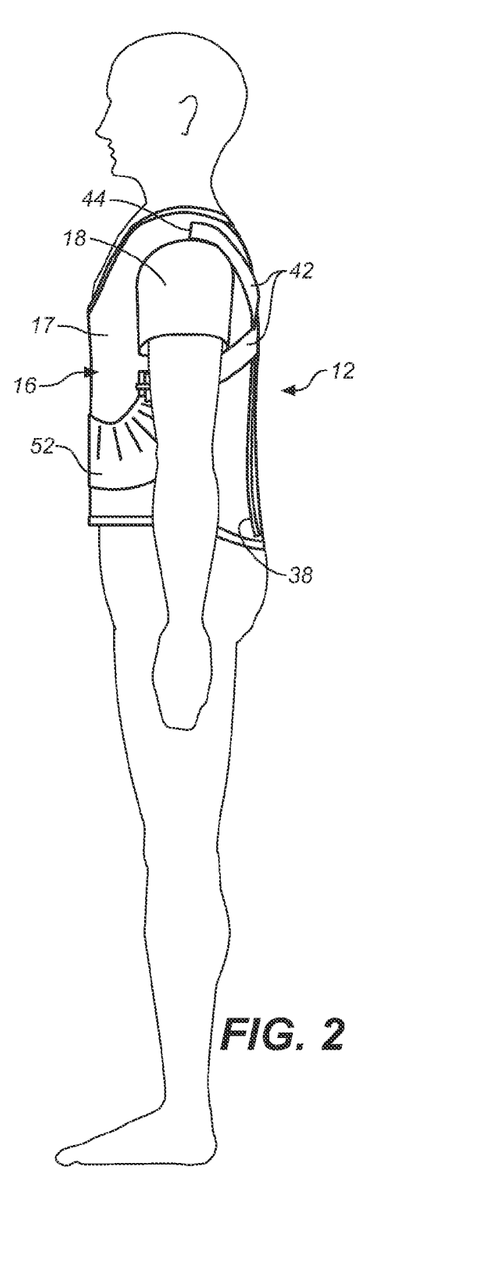
FIG. 2 is a side elevational view of the scapulo-spinal stabilizer shown in FIG. 1.
Figure 4A:
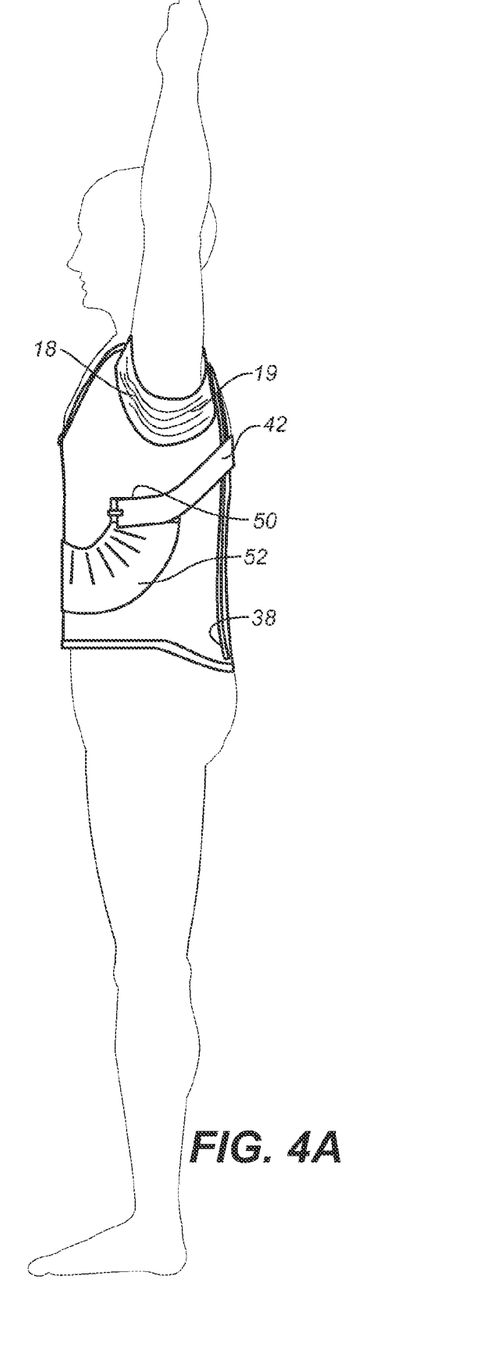
FIG. 4A is a side elevational view of the scapulo-spinal stabilizer similar to FIG. 2 with the individual's arms in elevated position revealing sleeve and side details of one of the cross straps.
Figure 4B:
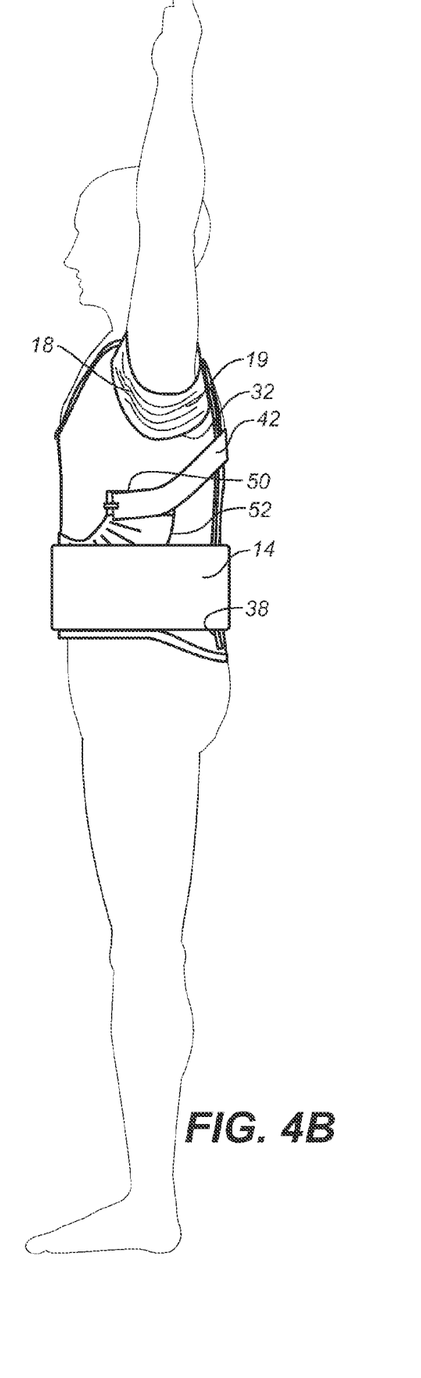
FIG. 4B is a rear elevational view of the scapulo-spinal stabilizer similar to that shown in FIG. 4A but with the waist band shown in FIG. 3B.

Each sleeve 18 is provided with a redundant sleeve closure 32 comprising a portion of gathered material 19 in the underpart of the sleeve to facilitate a full range of movement of the arms such as from the lowered position shown in FIG. 2 to the upwardly rotated position shown in FIGS. 4A and 4B. The redundant sleeve closure 32 splits the torque applied posterior to the shoulder, thus avoiding pressure on the lateral border of the pectoralis minor muscles at the anterior axillary line. The redundant anterior sleeve closure redistributes the posterior torque above and below the axilla in the mid-axillary line, thus diverting pressure on the pectoralis minor muscle on each side.

With reference now to FIG. 5B, two vertical, parallel, flexible, posterior, paramedian, thoraco-lumbar support stays 34 are removably held in dual sheaths 36 extending between the neck opening 48 and waist opening 51 in posterior panel 38 of the garment 16. See also FIGS. 3A and 3B. Each sheath 36 has a top opening 40 for insertion and removal of stays 34. The sheaths 36 closely hold the support stays 34 paramedially along each side of the spine. Support stays 34 link and stabilize the thoracolumbar junction of the spine while maintaining a neutral lumbar curve in continuity with the normal thoracic kyphosis. Contiguous, long-axis support does not sacrifice thoracic rotation or lumbar side-bending. The stays 34 cross the medial border of each scapula thus helping to overcome winging or elevation of the medial borders scapular due to periscapular muscular weakness caused by compromised nerve supply to the scapular stabilizing muscles.

Figure 5C:
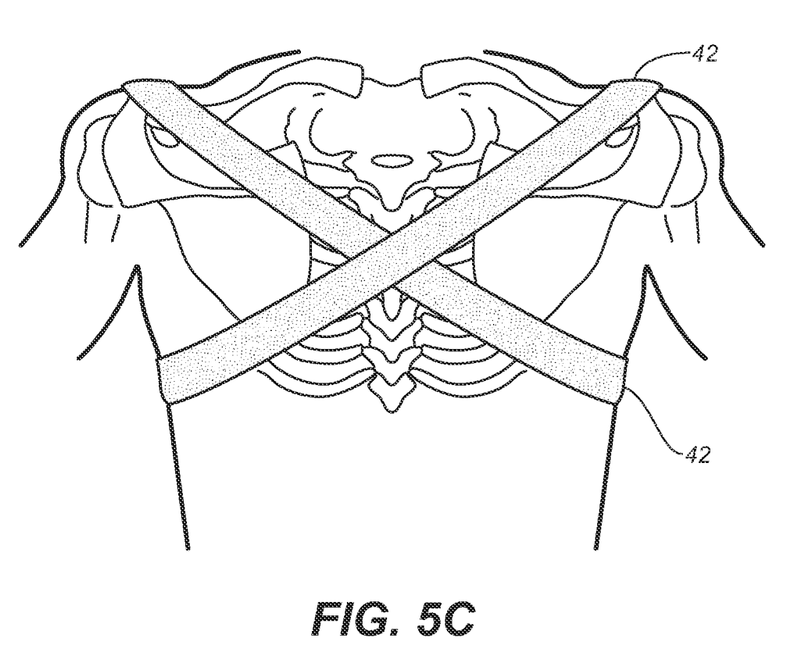
FIG. 5C is a rear view showing the scapular cross straps depicted in FIG. 5B arranged in an exemplary orientation over the anatomy surrounding the superior thoracic aperture.

Two posterior elastic, scapular straps 42 simultaneously cross the top part of the vertical stays and the shoulder blades. Each strap 42 anchors at anchor points 44 on the distal portion of the superior shoulder portion of the garment at superior shoulder seam 46 (see FIG. 5A) which, when the garment is being worn, locates the anchor point 44 posterior to the midcoronal plane immediately posterior and slightly proximal to the A-C joint at the superior border of the trapezius muscle. See, generally, FIG. 5C. The strap 42 is thus attached above and off the sleeve 18. This placement of the anchor point 44 also prevents "bunching" of the shoulder portion of the garment upon closure or tightening of the posterior cross straps 42 as discussed below. In the illustrated embodiment the superior shoulder seam 46 extends from the neck opening 48 to the sleeve 18 at the A-C joint. The superior shoulder seams 46 are stiffened by shoulder stays 49 residing in pockets 45 extending laterally from the neck opening 17. See FIG. 5A. Each pocket 45 is formed under and enclosed by one of the superior shoulder seams 46. Those of skill in the art will recognize that the locations of seams in the garment may be modified from the locations shown in the illustrations.

Figure 3A:
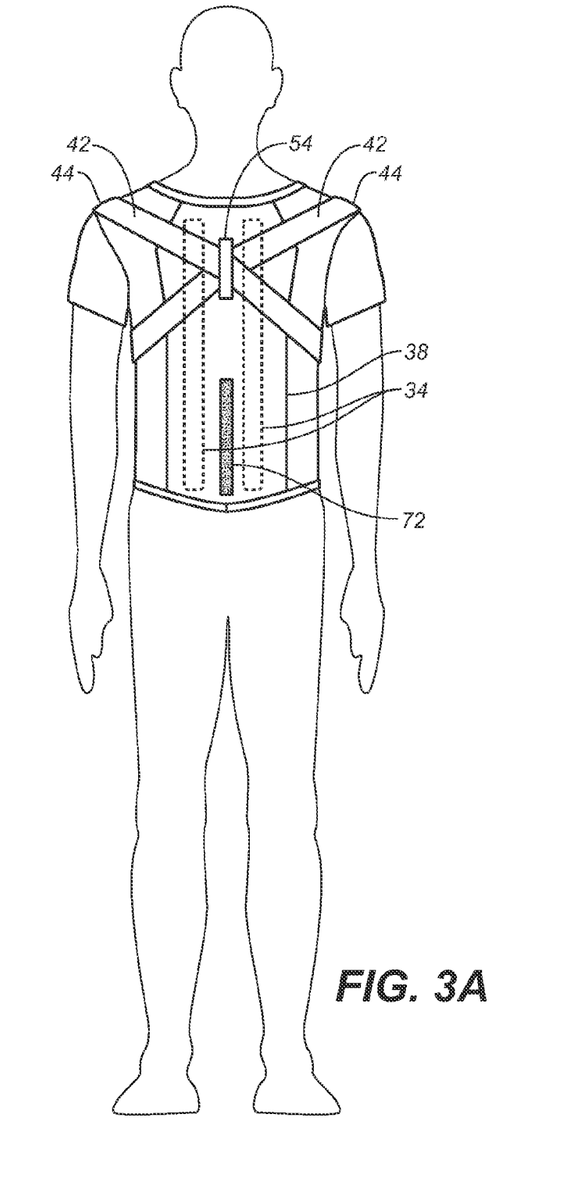
FIG. 3A is a rear elevational view of the scapulo-spinal stabilizer shown in FIG. 1.
Figure 3B:
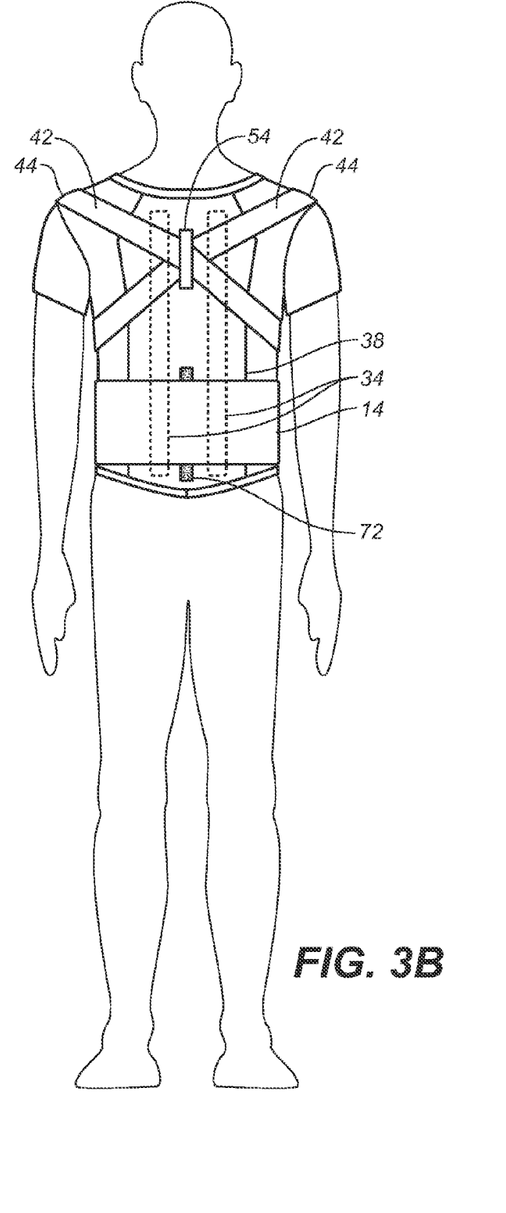
FIG. 3B is a rear elevational view of the scapulo-spinal stabilizer similar to that shown in FIG. 3A but with an added waist band.
Figure 7:
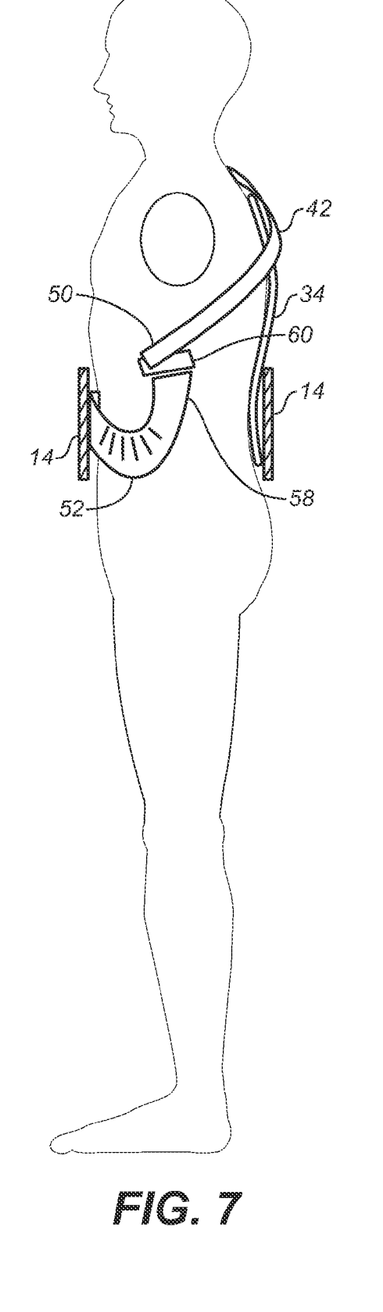
FIG. 7 is a side elevational view of a scapulo-spinal stabilizer similar to FIGS. 4A and 4B with the waist band shown in sectional view.

From anchor point 44 each strap 42 extends angularly downward, each strap 42 crossing the other to form an X-shaped configuration as seen in FIGS. 3A and 3B, toward the opposite side of the garment where its anterior end 50 is detachably connected with the anterior, inferior rib margin support 52. See also FIG. 7. Each strap 42 passes through a positioning loop 54 which helps keep straps 42 in relative position across the back of the garment. An easily gripped finger tab or loop 56 is provided on the anterior end of each strap 42 to facilitate holding onto and pulling the strap 42 to attach it to one of the anterior rib margin supports 52. The anterior end 50 of each strap 42 and the posterior end 58 of each anterior rib margin support 52 have cooperating hook-and-loop type fasteners 60 to permit adjustable fastening of straps 42 to rib margin supports 52.

Figure 8:
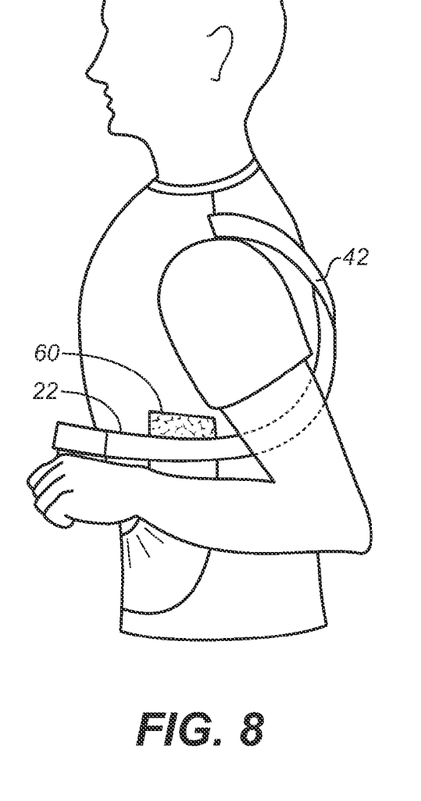
FIG. 8 is a side elevational view of an individual holding the pull tab at the anterior end of one of the scapular cross straps used to adjust tension in the cross straps.

After the wearer dons the garment, he or she pulls the tab 56 away from the body to clear it and then moves the end of the strap towards the front of the rib cage to increase tension in the straps, or posteriorly toward the back to reduce tension, as shown in FIG. 8. The straps can be adjusted independently depending on the anatomical and comfort needs of the wearer.

The anterior rib margin support 52 is attached to the lower part of the garment and comprises mirroring left and right halves $52_L$ and $52_R$ (see FIG. 5A) which are joined together by zipper 20 to form a contiguous unit for extending across the inferior anterior rib margin. See also FIG. 1. Each half $52_L$, $52_R$ comprises an upward sweeping, pleated, curved band 54 extending from a substantially horizontal medial end 57 disposed at the medial plane to a substantially vertical lateral end 58 on each side of the garment. The anterior ends 50 of the scapular straps 42 are attached to the lateral ends 58 of the anterior rib margin support 52. The anterior rib margin support 52 is composed of a sturdy elastic material. The elasticity of support 52 creates a cupping effect, which "grips" and supports the bony and cartilaginous anterior portions of the last three or four inferior rib margins, including the xiphisternum and the sternal body, thus moving the inferior rib margin cephalad (towards the head) in response to tension applied by tightening of straps 42. See FIGS. 1 and 2.

The purpose of the anterior rib margin support 52 upon application of tension is to increase the angle between the posterior rib cage and the thoracic spine. This angle can be shown on MRI or CT scans of the thorax to be abnormally acute (drooping toward the feet while sitting or standing) due to deconditioning or paralysis of peri-scapular and rib cage musculature, thus mechanically compromising respiration. A more obtuse rib angle promotes greater rib motion, thus increasing air exchange without increasing respiratory effort.

Figure 6:
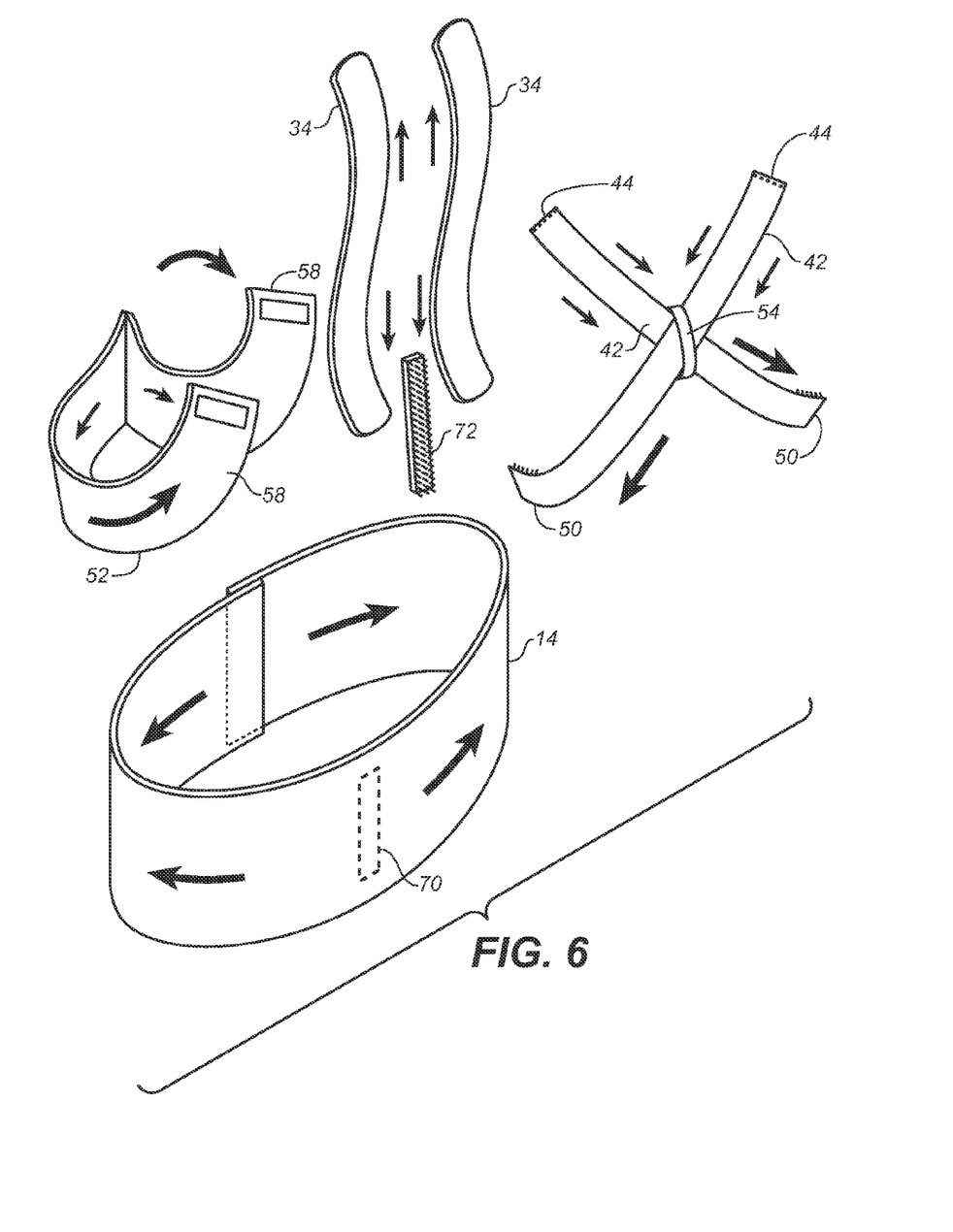
FIG. 6 is an upper perspective exploded view of certain elements of the scapulo-spinal stabilizer shown in FIGS. 5A and 5B.

Once the straps 42 are attached to the anterior rib margin support 52 as described above, a contiguous band is formed extending from each sleeve 18 and strap anchor point 44 across the back, around the side to and across the anterior, inferior abdomen. Tension exerted on the anterior rib margin support 52 by the wearer's abdomen and inferior rib cage is thus translated to straps 42 which pull back the distal superior shoulder portion of the garment at anchor points 44. Since anchor points 44 are located immediately behind and slightly proximal to the A-C joint, as discussed above, tension on straps 42 adducts the scapulae which rotate the clavicles forward by using the A-C joint as a pivot, thereby opening the superior thoracic apertures. Conversely, tension exerted on straps 42 is translated to the anterior rib margin support 52 which cups and supports lower portions of the rib margins, xiphisternum and sternal body moving the same cephalad and opening the angle between the posterior rib cage and the thoracic spine. See FIG. 6. Both salutary objectives are obtained without the device compressing structures on or around the superior thoracic apertures as in the prior art, and while facilitating a full range of arm motion.

Figure 11:
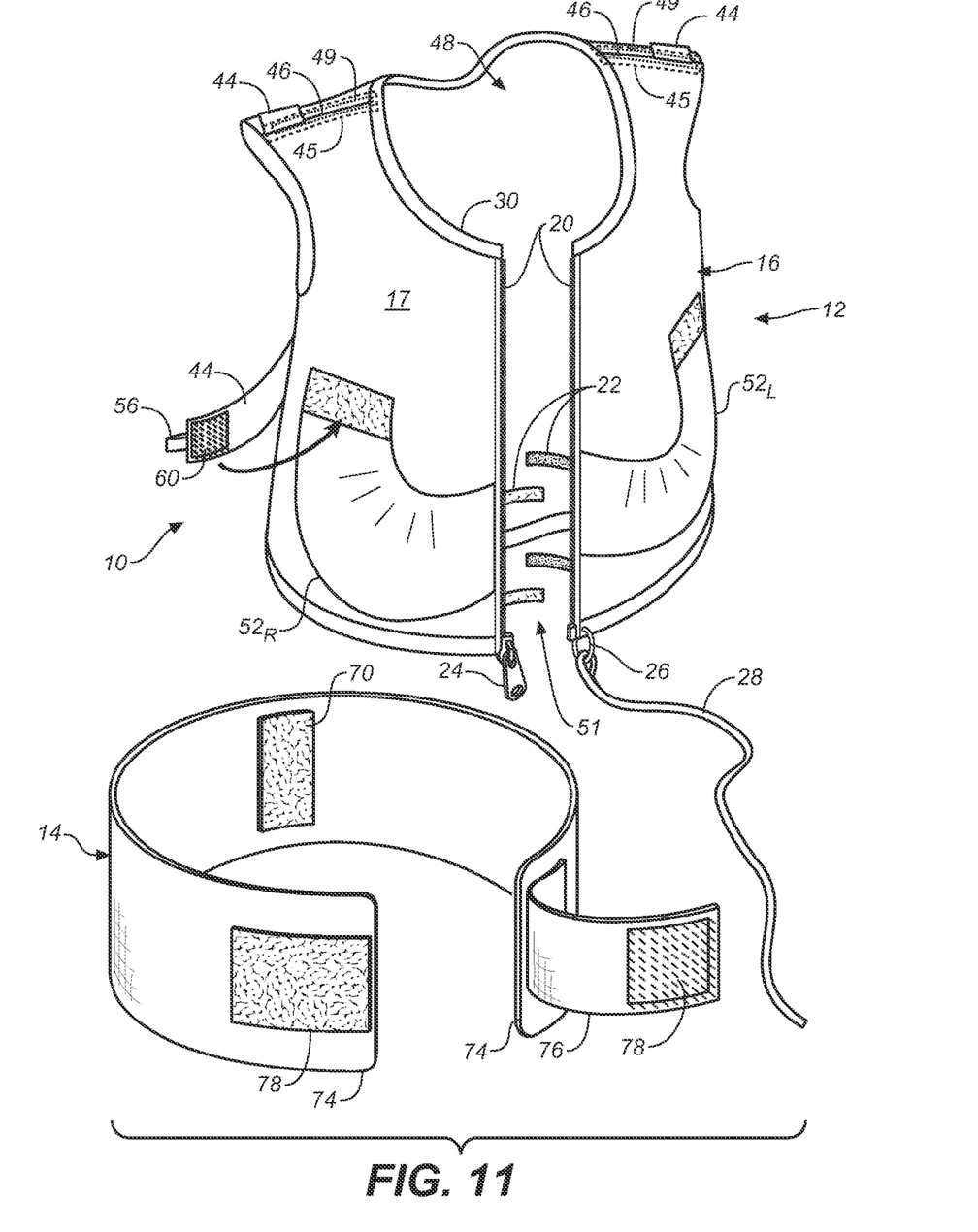
FIG. 11 is a front elevational view of another embodiment of a scapulo-spinal stabilizer in which the sleeves of the vest have been omitted.

FIG. 11 shows an embodiment of the invention as discussed above but in which the optional sleeves have been omitted from the vest 12.

In one embodiment of the invention, the optional zipper leash 28 has a snap ring 27 that can be attached to the ring 26 of the vest 12 as shown in FIG. 5A. The zipper leash 28 is long enough to be dropped to the floor whereupon a person who has donned the vest may step on the zipper leash 28 to stabilize the zipper 20 to facilitate its closing against the elastic resistance of the vest material. The zipper leash 28 may then be detached, or left attached, and stored inside the waist band 14 discussed next.

The optional waist band 14 is broad enough to wrap around and hold the wearer's lower abdomen without discomfort. It is detachable and secured to the back of the vest 12 by attaching one part of a hook-and-loop type fastener 70 (see FIG. 5A) on the band 14 to a vertical cooperating hook-and-look fastener strip 72 on the back side of the vest 12 (see FIG. 3A). The front ends 74 of the waist band 70 are closed together using a waist band strap 76 (FIG. 5A) which extends and overlaps the front ends 74 and is secured by using hook-and-loop type fastener 78. In one embodiment of the device the hook-and-loop type fastener 78 is offset relative to midline sufficiently that any free portion of waist band strap 76 does not distort overlying clothing at the front of the waist which might otherwise be noticeable. Use of waist band 14 is recommended but optional. However, if worn, it supports the abdominal muscles, thus creating improved truncal stability. It also helps prevent the tendency of vest 12 to ride up, particularly in persons with large abdomens, thus reducing efficiency of the garment.

In another embodiment of the invention, a brachial plexus-protecting elbow sling can attach to either side of the garment posterior to the mid-coronal, superior shoulder seam. A single, hook-and-loop type fastener (not illustrated) crossing the upper trapezius area from one side to the other serves as the point of attachment of the plexus sling. The sling is a fabric elbow "cuff" that attaches with a hook-and-loop type fastener to the trapezius anchor strip by a moveable but non-elastic, not-extendable band that attaches to the trapezius anchor with a single strap which adjusts with a pull tab that passes through a clip that allows the wearer to shorten or lengthen the support for the elbow cup. This feature allows the wearer to control the amount of tension that is placed on the brachial plexus by the weight of the arm. Relieving tension on the brachial plexus (which immediately reduces pain and tingling in the affected arm) must be accomplished without compromising the antero-posterior (A-P) dimension of the superior thoracic aperture. Narrowing this aperture as happens in progressive postural failure increases pressure and friction on the brachial plexus and the subclavian vessels and lymphatics. This scapulo-spinal stabilizer increases the A-P diameter of the aperture because all the weight of the upper extremity is supported posterior to the acromio-clavicular joint and the mid-coronal plane. This configuration of weight-bearing facilitates adduction of the scapula on the ipsilateral side thereby enhancing anterior rotation of the clavicle. This means that the clavicle pivots anteriorly as much as is allowed by its attachment to the manubrium sternum. If such a feature is desired then the vest must be worn as an outer garment as the support straps for the elbow cup cannot pass through ordinary clothing.

A scapulo-spinal stabilizer with abdominal support according to the invention improves degraded posture, redistributes body weight in a normal fashion along the spinal axis, and helps correct pathologic postural problems without restricting normal function. A major benefit of the device is that it opens the superior thoracic aperture thereby preserving normal blood flow.

There have thus been described certain preferred embodiments of a scapulo-spinal stabilizer with abdominal support for opening the superior thoracic aperture. While preferred embodiments have been described and disclosed, it will be recognized by those with skill in the art that modifications are within the true spirit and scope of the invention. The appended claims are intended to cover all such modifications.

I claim:

1. A scapulo-spinal stabilizer comprising:
a shirt-like garment for extending from the upper torso to the iliac crest of a wearer thereof, said garment having a neck opening, a waist opening, superior shoulder portions, a posterior panel, and an anterior portion, said superior shoulder portions extending laterally from said neck opening, said posterior panel opposite said anterior portion, and said anterior portion having a front closure for fastening the garment around a wearer's torso,
two elongated, semi-rigid thoraco-lumbar support stays,
said posterior panel having dual, spaced apart, parallel sheaths extending between said neck opening and said waist opening, said support stays received in said sheaths thereby closely holding and positioning said support stays paramedially along each side of the spine of a wearer and such that said stays cross the medial border of each scapula of the wearer, and
two posterior flexible scapular straps attached to anchor points located distally on the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays.

2. The scapulo-spinal stabilizer of claim 1 further comprising:
sleeves extending distally from said superior shoulder portions, said sleeves formed for wrapping around the proximal portions of a wearer's arms.

3. The scapulo-spinal stabilizer of claim 1 wherein:
said front closure includes a zipper.

4. The scapulo-spinal stabilizer of claim 1 wherein:
said garment comprises a material selected from the group of an expansible polyurethane fabric and latex-embedded material.

5. The scapulo-spinal stabilizer of claim 1 wherein:
said superior shoulder portions of said garment each include a shoulder stay extending from said neck opening, said shoulder stay having a distal end, said anchor points overlaying the distal ends of said shoulder stays.

6. The scapulo-spinal stabilizer of claim 1 wherein:
the anterior end of each of said scapular straps includes a grippable finger tab to facilitate holding onto and pulling said scapular straps.

7. The scapulo-spinal stabilizer of claim 1 further comprising:
a waist band detachably fastened to the posterior panel of said garment for wrapping around and supporting a wearer's lower abdomen, said waist band having a sufficient breadth to wrap around and hold a wearer's lower abdomen without discomfort.

8. A scapulo-spinal stabilizer comprising:
a shirt-like garment for extending from the upper torso to the iliac crest of a wearer thereof, said garment having a neck opening, a waist opening, superior shoulder portions, a posterior panel, and an anterior portion, said superior shoulder portions extending laterally from said neck opening, said posterior panel opposite said anterior portion, and said anterior portion having a front closure for fastening the garment around a wearer's torso,
sleeves extending distally from said superior shoulder portions, said sleeves formed for wrapping around the proximal portions of a wearer's arms, and each of said sleeves having an underpart including a portion of gathered material forming a redundant sleeve closure,
two elongated, semi-rigid thoraco-lumbar support stays,
said posterior panel having dual, spaced apart, parallel sheaths extending between said neck opening and said waist opening for closely holding and positioning said support stays paramedially along each side of the spine of a wearer such that said stays cross the medial border of each scapula of the wearer, and
two posterior flexible scapular straps attached to anchor points located distally on the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays.

9. A scapulo-spinal stabilizer comprising:
a shirt-like garment for extending from the upper torso to the iliac crest of a wearer thereof, said garment having a neck opening, a waist opening, superior shoulder portions, a posterior panel, and an anterior portion, said superior shoulder portions extending laterally from said neck opening, said posterior panel opposite said anterior portion, and said anterior portion having a front closure for fastening the garment around a wearer's torso, said front closure including a zipper having a bottom portion and a flexible cord detachably attached to the bottom portion of said zipper, said cord having a length at least sufficient to extend from the bottom portion of said zipper to a ground surface such that it can be stepped on when said garment is being donned by a wearer
two elongated, semi-rigid thoraco-lumbar support stays,
said posterior panel having dual, spaced apart, parallel sheaths extending between said neck opening and said waist opening for closely holding and positioning said support stays paramedially along each side of the spine of a wearer such that said stays cross the medial border of each scapula of the wearer, and
two posterior flexible scapular straps attached to anchor points located distally on the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays.

10. A scapulo-spinal stabilizer comprising:
a shirt-like garment for extending from the upper torso to the iliac crest of a wearer thereof, said garment having a neck opening, a waist opening, superior shoulder portions, a posterior panel, and an anterior portion, said superior shoulder portions extending laterally from said neck opening, said posterior panel opposite said anterior portion, and said anterior portion having a front closure for fastening the garment around a wearer's torso, said front closure including a zipper,
said anterior portion of said garment having left and right sides meeting at said front closure, said left and right sides having at least one pair of laterally extending cooperating tabs, each of said at least one said pair of cooperating tabs having cooperating fasteners that can be detachably fastened together to secure the left and right sides of said anterior portion in spaced adjacent relation in preparation for closing said zipper,
two elongated, semi-rigid thoraco-lumbar support stays,
said posterior panel having dual, spaced apart, parallel sheaths extending between said neck opening and said waist opening for closely holding and positioning said support stays paramedially along each side of the spine of a wearer such that said stays cross the medial border of each scapula of the wearer, and
two posterior flexible scapular straps attached to anchor points located distally on the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays.

11. A scapulo-spinal stabilizer comprising:
a shirt-like garment for extending from the upper torso to the iliac crest of a wearer thereof, said garment having a neck opening, a waist opening, superior shoulder portions, a posterior panel, and an anterior portion, said superior shoulder portions extending laterally from said neck opening, said posterior panel opposite said anterior portion, and said anterior portion having a front closure for fastening the garment around a wearer's torso, said anterior portion of said garment including anterior rib margin supports, each said anterior rib margin support having a pleated curved band for extending over and supporting the inferior rib margins of a wearer of said garment, two elongated, semi-rigid thoraco-lumbar support stays, said posterior panel having dual, spaced apart, parallel sheaths extending between said neck opening and said waist opening for closely holding and positioning said support stays paramedially along each side of the spine of a wearer such that said stays cross the medial border of each scapula of the wearer, and two posterior flexible scapular straps attached to anchor points located distally on the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays.

12. The scapulo-spinal stabilizer of claim 11 wherein:
each said anterior rib margin support includes a substantially horizontal medial end and a substantially vertical lateral end.

13. The scapulo-spinal stabilizer of claim 12 wherein:
the anterior ends of said scapular straps detachably fastened to the lateral portions of said anterior rib margin supports.

14. A scapulo-spinal stabilizer comprising:
a shirt-like garment for extending from the upper torso to the iliac crest of a wearer thereof, said garment having a neck opening, a waist opening, superior shoulder portions, a posterior panel, and an anterior portion, said superior shoulder portions extending laterally from said neck opening, said posterior panel opposite said anterior portion, and said anterior portion having a front closure for fastening the garment around a wearer's torso, two elongated, semi-rigid thoraco-lumbar support stays, said posterior panel having dual, spaced apart, parallel sheaths extending between said neck opening and said waist opening for closely holding and positioning said support stays paramedially alongside each side of the spine of a wearer such that said stays cross the medial border of each scapula of the wearer, two posterior flexible scapular straps attached to anchor points located on the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays, and said anterior portion of said garment including anterior rib margin supports, each said anterior rib margin support including a pleated curved band for extending over and supporting the inferior rib margins of a wearer of said garment, each said anterior rib margin support including a substantially horizontal medial end and a substantially vertical lateral end, the anterior ends of said scapular straps detachably fastened to the lateral ends of said anterior rib margin supports.

15. A scapulo-spinal stabilizer comprising:
a shirt-like garment for extending from the upper torso to the iliac crest of a wearer thereof, said garment having a neck opening, a waist opening, superior shoulder portions, a posterior panel, an anterior portion, and sleeves, said superior shoulder portions extending laterally from said neck opening, said superior shoulder portions each including a shoulder stay extending from said neck opening, said shoulder stay having a distal end, said posterior panel opposite said anterior portion, and said anterior portion having a front closure for fastening the garment around a wearer's torso, said sleeves extending distally from said superior shoulder portions and formed for wrapping around the proximal portions of a wearer's arms, said sleeves each including an underpart and a portion of gathered material forming a redundant sleeve closure on said underpart of each of said sleeves, two elongated, semi-rigid thoraco-lumbar support stays, said posterior panel having dual, spaced apart, parallel sheaths extending between said neck opening and said waist opening, said support stays received in said sheaths thereby closely holding and positioning said support stays paramedially along each side of the spine of a wearer and such that said stays cross the medial border of each scapula of the wearer, and two posterior flexible scapular straps attached to anchor points located on the distal ends of the superior shoulder portions of said garment such that said anchor points are positioned posterior to the mid-coronal plane immediately posterior to the acromiclavicular joint at the superior border of the trapezius muscle of a wearer of the garment, said scapular straps each extending angularly downward from said anchor points towards the opposite side of the garment, each of said scapular straps having an anterior end, the anterior ends of said scapular straps detachably attached to the anterior portion of said garment so that said scapular straps form a crossing configuration across said posterior panel and said support stays.

* * * * *